(12) United States Patent
Pierce

(10) Patent No.: US 8,999,036 B2
(45) Date of Patent: Apr. 7, 2015

(54) METHOD FOR PRODUCTION OF A COMPRESSED NATURAL GAS EQUIVALENT FROM LANDFILL GAS AND OTHER BIOGASES

(71) Applicant: Jeffrey L. Pierce, Torrance, CA (US)

(72) Inventor: Jeffrey L. Pierce, Torrance, CA (US)

(73) Assignee: Stearns Conrad Schmidt Consulting Engineers, Inc., Long Beach, CA (US)

( * ) Notice: Subject to any disclaimer, the term of this patent is extended or adjusted under 35 U.S.C. 154(b) by 17 days.

(21) Appl. No.: 13/627,692

(22) Filed: Sep. 26, 2012

(65) Prior Publication Data

US 2013/0019633 A1 Jan. 24, 2013

(51) Int. Cl.
*B01D 53/22* (2006.01)
*C10L 3/08* (2006.01)
*B01D 53/00* (2006.01)
*B01D 53/04* (2006.01)
*C10L 3/10* (2006.01)
*C12M 1/00* (2006.01)

(52) U.S. Cl.
CPC .............. *C10L 3/08* (2013.01); *B01D 53/002* (2013.01); *B01D 53/04* (2013.01); *B01D 53/227* (2013.01); *B01D 53/229* (2013.01); *B01D 2253/102* (2013.01); *B01D 2256/245* (2013.01); *B01D 2257/30* (2013.01); *B01D 2257/304* (2013.01); *B01D 2257/504* (2013.01); *B01D 2257/708* (2013.01); *B01D 2257/80* (2013.01); *B01D 2258/05* (2013.01); *Y02C 10/08* (2013.01); *Y02C 10/10* (2013.01); *Y02E 50/346* (2013.01); *C10L 3/101* (2013.01); *C12M 47/18* (2013.01); *Y10S 95/901* (2013.01)

(58) Field of Classification Search
USPC ............... 95/45, 47, 50, 51, 90, 901; 96/4, 10
See application file for complete search history.

(56) References Cited

U.S. PATENT DOCUMENTS

| | | | |
|---|---|---|---|
| 5,642,630 A * | 7/1997 | Abdelmalek et al. | ........... 62/632 |
| 5,727,903 A | 3/1998 | Borray et al. | |
| 6,071,326 A * | 6/2000 | Hall | .................. 95/41 |
| 6,156,096 A * | 12/2000 | Sirkar | ................ 95/44 |
| 6,368,849 B1 * | 4/2002 | Norddahl | ....................... 435/262 |
| 6,601,543 B2 * | 8/2003 | Rautenbach et al. | ............. 123/3 |
| 7,005,068 B2 * | 2/2006 | Hoffland | ....................... 210/603 |
| 7,087,170 B2 * | 8/2006 | You et al. | ....................... 210/605 |
| 7,435,349 B2 * | 10/2008 | You et al. | ....................... 210/605 |
| 7,731,779 B2 | 6/2010 | Palumbo | |
| 7,815,713 B2 | 10/2010 | Sorensen et al. | |
| 7,972,082 B2 * | 7/2011 | Augenstein et al. | ..... 405/129.95 |
| 8,158,378 B2 * | 4/2012 | Mitariten | ....................... 435/29 |
| 8,480,789 B2 * | 7/2013 | Sorensen et al. | .................. 95/50 |
| 8,580,113 B2 * | 11/2013 | Hong et al. | ....................... 210/603 |
| 2002/0069838 A1 * | 6/2002 | Rautenbach et al. | ........ 123/25 A |
| 2005/0066815 A1 * | 3/2005 | Krushnevych et al. | .......... 96/108 |
| 2006/0213370 A1 | 9/2006 | Leonard et al. | |
| 2006/0243661 A1 * | 11/2006 | You et al. | ....................... 210/605 |

(Continued)

FOREIGN PATENT DOCUMENTS

WO WO 9509105 A1 * 4/1995

*Primary Examiner* — In Suk Bullock
*Assistant Examiner* — Anthony Shumate
(74) *Attorney, Agent, or Firm* — Davis & Bujold, PLLC; Michael J. Bujold

(57) ABSTRACT

Biogas is converted to a vehicle fuel equivalent to compressed natural gas high in methane in a simple, low cost process involving steps of refrigeration, non-regenerative activated carbon purification and carbon dioxide removal using low-pressure membrane technology.

5 Claims, 2 Drawing Sheets

(56) References Cited

U.S. PATENT DOCUMENTS

| | | | |
|---|---|---|---|
| 2009/0156875 A1* | 6/2009 | Tomioka et al. | 585/802 |
| 2009/0282882 A1* | 11/2009 | Verhave et al. | 71/7 |
| 2010/0248335 A1* | 9/2010 | Komatsu et al. | 435/262.5 |
| 2010/0264079 A1* | 10/2010 | Begin et al. | 210/603 |
| 2011/0023497 A1* | 2/2011 | Assmann | 60/780 |
| 2011/0023710 A1* | 2/2011 | Sorensen et al. | 95/50 |
| 2011/0296809 A1 | 12/2011 | Brotherton et al. | |
| 2012/0175236 A1 | 7/2012 | Lee | |
| 2014/0014577 A1* | 1/2014 | Wakahara et al. | 210/603 |

* cited by examiner

METHOD FOR PRODUCTION OF A COMPRESSED NATURAL GAS EQUIVALENT FROM LANDFILL GAS AND OTHER BIOGASES

This invention relates to the conversion of landfill gas and other biogases to a compressed natural gas equivalent.

BACKGROUND OF THE INVENTION

Compressed natural gas (CNG) is seeing increased use as a vehicle fuel in the United States and worldwide. CNG can also be utilized for heating and other uses where natural gas pipelines do not exist. Large quantities of biogas (landfill gas, digester gas, anaerobic wastewater treatment process gas and other biogases) are currently being flared to the atmosphere. Biogas is flared when it cannot be utilized economically for on-site power production or where other traditional markets for biogas do not exist. It would be good for both the environment and the economy to convert combustible gases now being flared to a useful form of energy.

The current invention converts biogas to a CNG equivalent. It differs from and is an improvement to the Borray U.S. Pat. No. 5,727,903 for conversion of landfill gas into a CNG equivalent in that the current invention employs a simpler, less costly process chain. The process of the current invention can be scaled down more practically and economically to much smaller sized processing plants, allowing smaller sources of biogas to be exploited.

Biogas, when converted into a natural gas equivalent, and then to a CNG equivalent or a liquefied natural gas (LNG) equivalent, is considered to be what is known as biomethane. Biomethane is a renewable fuel and can be used by producers and users of fossil vehicle fuels to meet renewable fuel utilization goals and/or greenhouse gas reduction goals. Biomethane CNG (B-CNG) commands a premium both environmentally and economically in the vehicle fuel market.

CNG vehicle fuel standards have been established by the California Air Resources Board (CARB) and others. Biogas does not comply with many of the line item specifications in these standards. The methane content of biogas is too low. The carbon dioxide, and sometimes the nitrogen content, of biogas is too high. The moisture content of biogas is too high. The sulfur content of biogas is too high. While compliant with the specifications governing volatile organic compounds (VOCs), certain biogases contain individual VOCs which must be removed (despite not being specifically listed in CNG vehicle fuel specification standards), such as siloxane compounds, as these compounds are known by those in the biogas industry to be harmful to reciprocating engines.

Converting biogas to a CNG equivalent requires: 1) limiting nitrogen at the source of the biogas; 2) dehydration; 3) removal of carbon dioxide; 3) removal of VOCs; 4) removal of sulfur compounds; and 5) compression.

SUMMARY OF THE INVENTION

The current invention employs refrigeration for bulk moisture removal, non-regenerative media for VOC removal and sulfur compounds removal, and a single-stage membrane for carbon dioxide removal and further moisture and hydrogen sulfide removal.

The process of the current invention recovers only about 65 percent of the inlet methane as product methane. At most sites, an abundance of biogas will remain unused and percent methane recovery is irrelevant. At sites which have a contemporaneous biogas utilization system, the waste gas stream (at about 30 percent methane) might be blended with the biogas being used by that utilization system. In addition, if sufficient waste gas is available, the waste gas can be used to generate power in a new microturbine or other type of power generation system. The cost savings associated with installing and operating a simplified process chain justifies the reduction in methane recovery. If this is not the case, at a particular location, then a second stage of membranes plus gas recycle can be added to increase methane recovery to at least 85 percent.

In a typical low methane recovery system, the inlet biogas flow might be 350 standard cubic feet per minute (scfm) at 54.9 percent methane. Using this invention, the B-CNG production would be 132 scfm at 95.3 percent methane (equivalent to 1470 gallons of gasoline per day), and the waste gas flow would be 218 scfm at 30.5 percent methane. The waste gas, in this instance, could fuel a 250 kW microturbine.

In a high methane recovery system, the inlet flow on landfill gas might be 520 scfm at 54.9 percent methane. With this invention, the B-CNG production would be about 256 scfm at 95.1 percent methane, producing 2,840 gallons of gasoline equivalent of B-CNG per day. The waste gas flow would be 264 scfm at 16.0 percent methane. The low methane content of the waste gas requires that the waste gas be incinerated in a special waste gas flare or a special microturbine that accepts very low-Btu content gas.

The low methane recovery embodiment of this invention differs from the invention in the Borray U.S. Pat. No. 5,727,903 in the following ways:

The Borray system utilizes a complex, thermally regenerative system for VOC removal. The current invention employs a simple non-regenerative activated carbon system for VOC removal. The approach employed by the current invention requires less maintenance, consumes less power, has a lower capital cost, and is more reliable;

The current invention employs low pressure (120 psig) membranes, while the Borray system employs high pressure (1,000 psig) membranes. The lower operating pressure of the current invention reduces power consumption;

The current invention employs one stage of membranes, while the Borray system employs two stages of membranes in series. A one stage system has a lower capital cost and less operating complexity; and The Borray system incorporates recycle of second stage membrane permeate, requiring recompression of the permeate, along with the inlet biogas. The current invention does not recycle permeate; as a consequence, the current invention requires less power to operate.

The high methane recovery embodiment of this invention differs from the invention in the Borray U.S. Pat. No. 5,727,903 in the following ways:

The Borray system utilizes a complex, thermally regenerative system for VOC removal. The current invention employs a simple non-regenerative activated carbon system for VOC removal. The approach employed by the current invention requires less maintenance, consumes less power, has a lower capital cost, and is more reliable; and The current invention employs low pressure (120 psig) membranes, while the Borray system employs high pressure (1,000 psig) membranes. The lower operating pressure of the current invention reduces power consumption.

DETAILED DESCRIPTION

Figure 1:
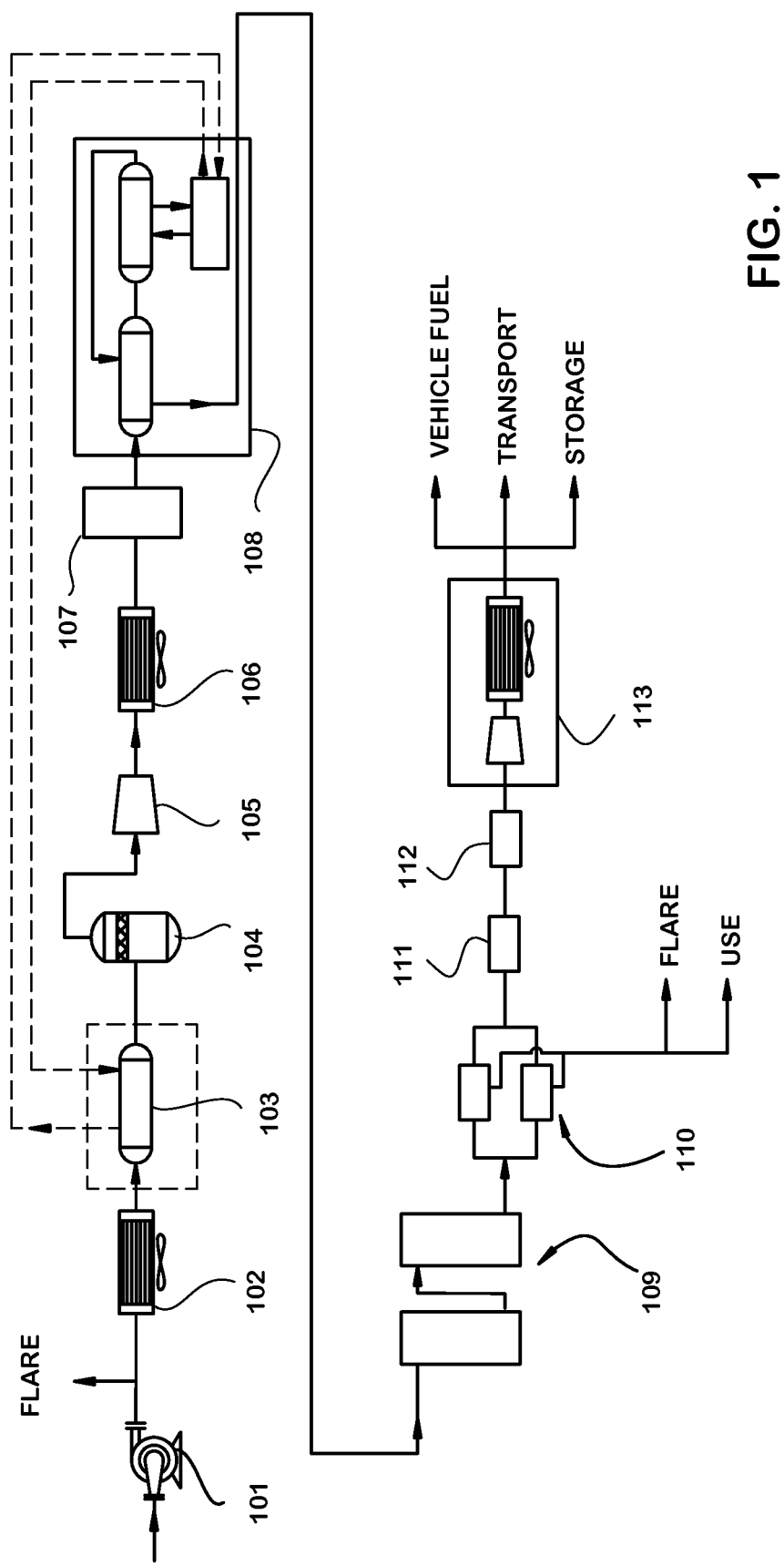
FIG. 1 illustrates the a methane recovery system embodying the invention.

FIG. 1 illustrates the basic invention in its low methane recovery configuration.

As shown in FIG. 1, a blower 101 draws from a source of biogas (e.g., landfill gas wells) and supplies an initial stage of pressurization for the B-CNG facility. If the biogas source is already at sufficient pressure, the blower may be eliminated. In landfill gas applications, it will often be necessary to connect only the best quality wells (those with the lowest nitrogen and oxygen content) to the B-CNG facility. The vacuum/booster blower will serve as the source of vacuum for the landfill gas collection piping dedicated to these wells. The blower is preferably of the centrifugal type, but it could instead be a rotary positive displacement type device.

Downstream of the blower, an air-to-gas cooler 102 reduces the heat of compression generated by the blower 101. The air-to-gas cooler is preferably a fin-fan type heat exchanger.

An optional chilled-water-to-gas heat exchanger 103 may be used, depending on the type of compressor 105, described below, and the need to prevent the accumulation of water in its compressor oil. The heat exchanger can be a shell and tube type, plate and frame type, or other type of heat exchanger which cools the biogas to 40° F. to 70° F. using chilled water. The source of the chilled water is component 108, described below.

A moisture separator 104 then removes water from the biogas, produced as a result of temperature reduction by components 102 and 103.

A compressor 105 compresses the biogas to a pressure of about 120 psig, for further processing in the B-CNG facility. A flooded screw-type, rotary vane-type, scroll-type or other type compressor can be employed.

Next, an air-to-gas heat exchanger 106 removes the heat of compression generated by compressor 105. The air-to-gas cooler is preferably a fin-fan type heat exchanger.

The sulfur compounds removal unit 107 is an optional component, required only if the concentration of sulfur compounds in the biogas exceeds 50 parts per million volumetric (ppmv) as hydrogen sulfide. A subsequent component 109 can remove sulfur compounds in addition to VOCs; however, a separate sulfur compounds removal unit greatly increases the life of the media in component 109, when the concentration of sulfur compounds is elevated. Pretreatment for sulfur compounds can reduce the overall operating cost of the B-CNG facility.

The preferred sulfur compounds removal unit 107 is a vessel (stainless steel or carbon steel suitably lined) which contains a commercially available media for sulfur compounds removal (e.g., SulfaTreat, Sulfa-Rite). Once the media is spent, it is replaced.

The compressed gas now enters a chilling\reheating unit 108, which cools the gas to the range of 40° F. to 50° F., using a chilled water-to-gas heat exchanger, and then reheats it by about 30° F., using a gas-to-gas heat exchanger (located upstream of the chilled water-to-gas heat exchanger).

The chilled water is supplied by a conventional industrial or commercial duty chiller. The heat exchangers can be shell-and-tube type or other types of heat exchangers. The purpose of the chilling/reheating unit 108 is to produce a biogas with a relative humidity of less than 80 percent and a temperature less than 80° F.

A VOC removal device 109 includes two vessels in series (carbon steel suitably lined), filled with activated carbon. The activated carbon type is a selected blend based on the impurities in the biogas to be treated. Once the activated carbon is spent, it is replaced with new activated carbon. The vessels can be arranged in a permanent lead-lag configuration or in a reversible lead-lag configuration, by adding more piping and valves. FIG. 1 shows a permanent lead-lag configuration.

Downstream of the VOC removal device 109, one or more membrane gas separator modules 110 are installed in parallel. Commercially available low pressure (120 psig) hollow fiber counter-current membrane modules (e.g., Air Liquide Biogaz membranes) are used to separate methane from undesirable gases. Gas separation occurs because different gases pass through the membrane wall at different rates. Methane is a slow gas. The methane is retained for the product gas (so-called residual gas). Certain other gases (carbon dioxide, water, hydrogen sulfide and some oxygen), undesirable gases, pass through the membrane wall and become a waste gas stream (so-called permeate gas). The permeate gas in the single stage membrane configuration has a methane content of about 30 percent. The permeate gas can be disposed of in a new or existing flare, or used in existing biogas utilization equipment or used in new biogas utilization equipment, such as a microturbine.

A methane analyzer 111 continuously analyzes the methane content of the biomethane to assure that it does not drop below the minimum percentage required to meet CNG standards.

Component 112 adds a mercaptan to the biomethane, giving it the distinctive smell of natural gas.

Finally, the gas is compressed by a compressor 113 to 3,000 to 4,500 psig for direct dispensing into vehicles, for delivery into stationary tube storage, or for delivery to tube trailers for off-site transport. This compressor is typically a reciprocating type compressor. The product gas can also be directed to an LNG production step.

While typical applications for this invention are small in size, there may be larger applications where a higher percentage methane recovery is desired.

Figure 2:
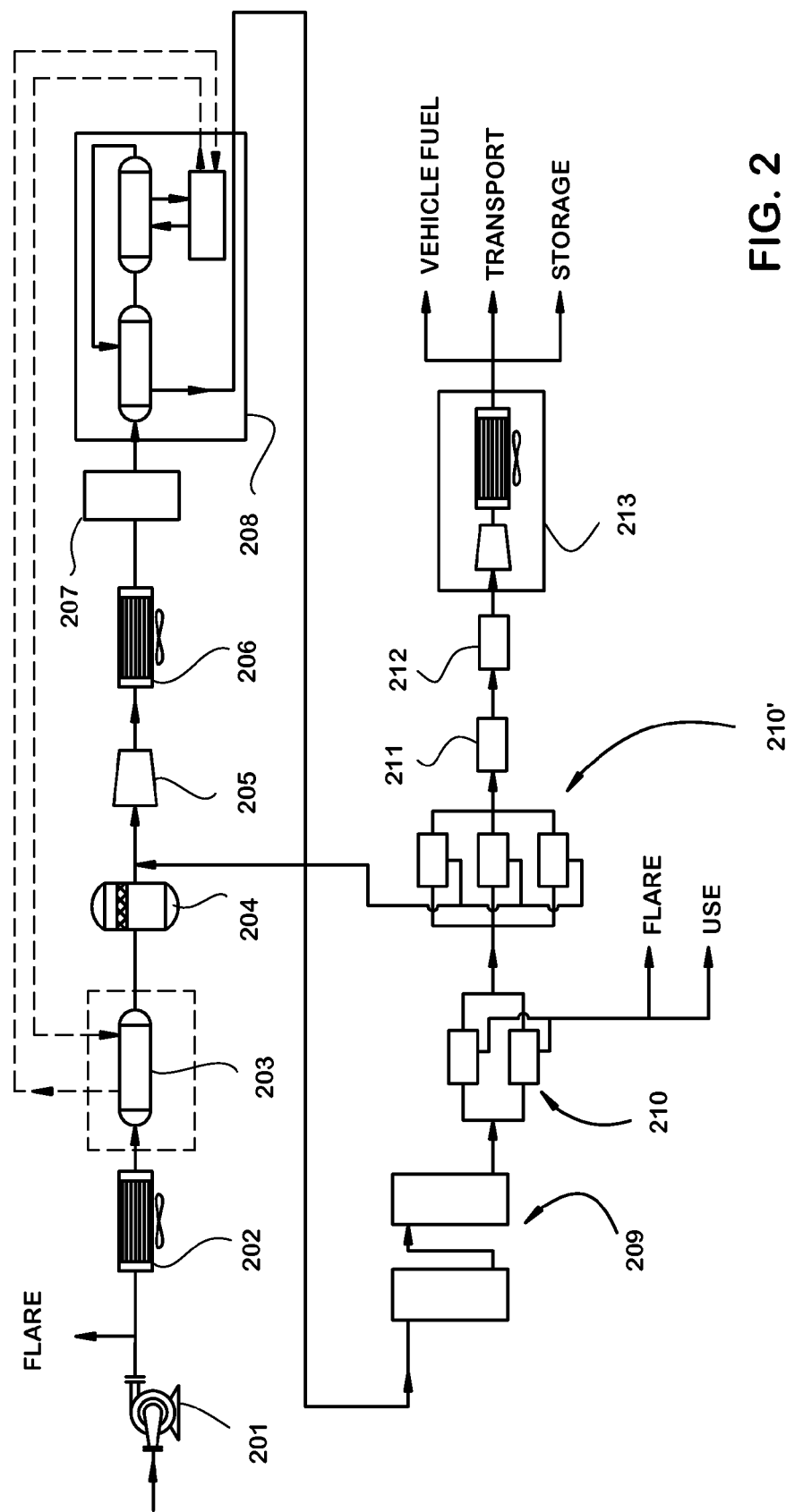
FIG. 2 illustrates a modified form of the invention in a high methane recovery configuration.

FIG. 2 illustrates the invention in its high methane recovery embodiment. In FIG. 2, reference numbers differ by one hundred from the reference numbers of corresponding components in FIG. 1.

The system of FIG. 2 shares many of the components of FIG. 1; those have the functions indicated above, except as described below.

In this embodiment, there are two stages of membrane modules 210, 210' to improve methane recovery. In the first stage 210, the membrane modules are arranged in parallel. The permeate gas from the second stage of membranes 210' has a methane content of about 60 percent, and is recycled to the head of compressor 205. The second stage increases methane recovery to 85 percent. Thus, by adding a second stage of membrane modules, efficiency is increased with respect to the first embodiment of the invention described above.

Inasmuch as the invention is subject to variations and changes in detail, it is intended that the foregoing should be regarded as merely illustrative of the invention defined by the claims below.

What is claimed is:

1. A method for converting landfill gas and other biogases into a compressed biomethane for use as fuel, said method comprising steps of:

drawing biogas from a biogas source, then
pressurizing the biogas, then
chilling the biogas to 40° F. to 70° F., then
separating condensed water from the biogas, then
compressing the biogas to about 120 psig, then
cooling the biogas, then
dehumidifying the biogas, then
removing volatile organic compounds from the biogas by passing it through a non-regenerative activated carbon bed, then
passing the biogas through a gas separator having a membrane which preferentially removes gases other than methane from the biogas, thus producing a gas having a methane content higher than that of the biogas, and then
compressing and storing the gas.

2. The method of claim 1, further comprising a step of removing sulfur compounds from the gas.

3. The method of claim 2, wherein the step of removing sulfur compounds immediately follows the compression and cooling steps, and immediately precedes the dehumidifying step.

4. The method of claim 1, wherein the dehumidifying step comprises cooling the biogas to 40° F. to 50° F., and then reheating it to produce a biogas with a relative humidity of less than 80 percent at a temperature less than 80° F.

5. The method of claim 1, wherein the step of compressing the gas raises the pressure of said gas to 3,000 to 4500 psig.

\* \* \* \* \*